United States Patent [19]

McGill et al.

[11] Patent Number: 4,603,703
[45] Date of Patent: Aug. 5, 1986

[54] METHOD FOR REAL-TIME DETECTION AND IDENTIFICATION OF NEUROELECTRIC SIGNALS

[75] Inventors: Kevin C. McGill, Palo Alto; Leslie J. Dorfman, Stanford, both of Calif.

[73] Assignee: The Board of Trustees of the Leland Stanford Junior University, Stanford, Calif.

[21] Appl. No.: 599,889

[22] Filed: Apr. 13, 1984

[51] Int. Cl.⁴ .............................................. A61B 5/04
[52] U.S. Cl. .................................. 128/731; 128/733; 364/417
[58] Field of Search ................ 364/417, 415; 128/731, 128/733

[56] References Cited

U.S. PATENT DOCUMENTS

| | | | |
|---|---|---|---|
| 3,606,882 | 9/1971 | Abe et al. ............................. | 128/703 |
| 3,616,791 | 11/1971 | Harris ................................. | 128/702 |
| 3,658,055 | 4/1972 | Abe et al. ............................ | 128/703 |
| 3,940,692 | 2/1976 | McEwan et al. ................. | 128/702 X |
| 4,254,779 | 3/1981 | Miyata et al. ........................ | 128/731 |
| 4,416,288 | 11/1983 | Freeman ............................. | 128/731 |
| 4,417,592 | 11/1983 | John ..................................... | 128/731 |

OTHER PUBLICATIONS

James D. Frost, Int. J. Bio-Medical Computing, (10), No. 5, pp. 357-373, (1979).
Arthur, J. Lim et al., IEEE Trans. on Biomedical Engineering, BME-27, No. 4, pp. 212-220, Apr. 1980.
S. Johansson et al., Med. & Biol. Engng., vol. 8, No. 3, pp. 257-264, (1970).

Primary Examiner—G. L. Kaplan
Attorney, Agent, or Firm—Flehr, Hohbach, Test Albritton & Herbert

[57] ABSTRACT

Neuroelectric signals are detected and processed by digital filtering to detect, classify and determine the relative proportions of the different types of signals eminating from muscle, nerve or brain tissue.

21 Claims, 13 Drawing Figures

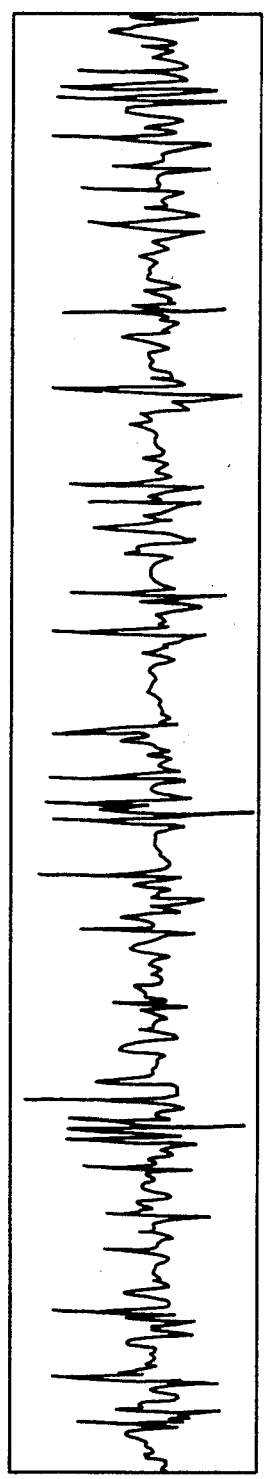
FIG_1A
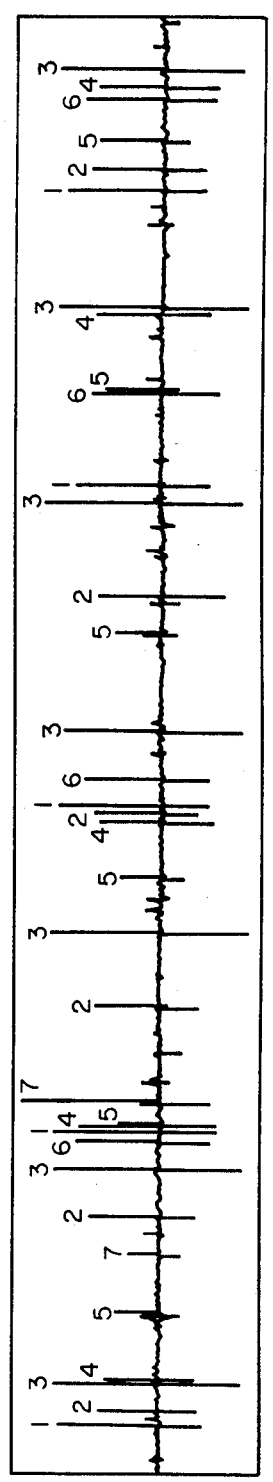
FIG_1B

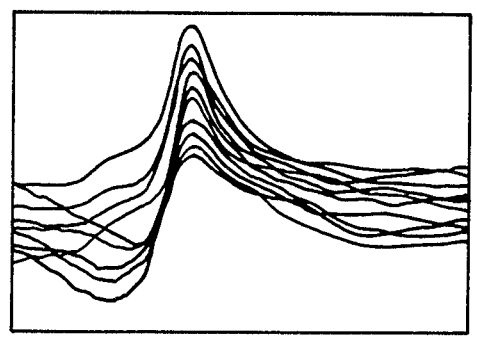
FIG_2A
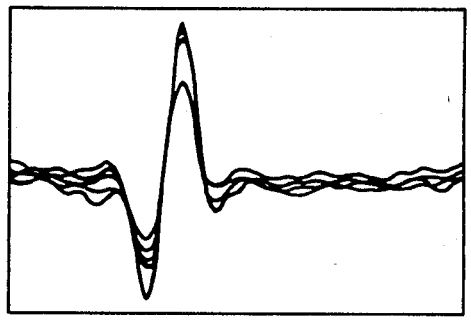
FIG_2B
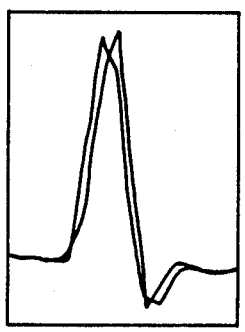  
FIG_3A  FIG_3B  FIG_3C

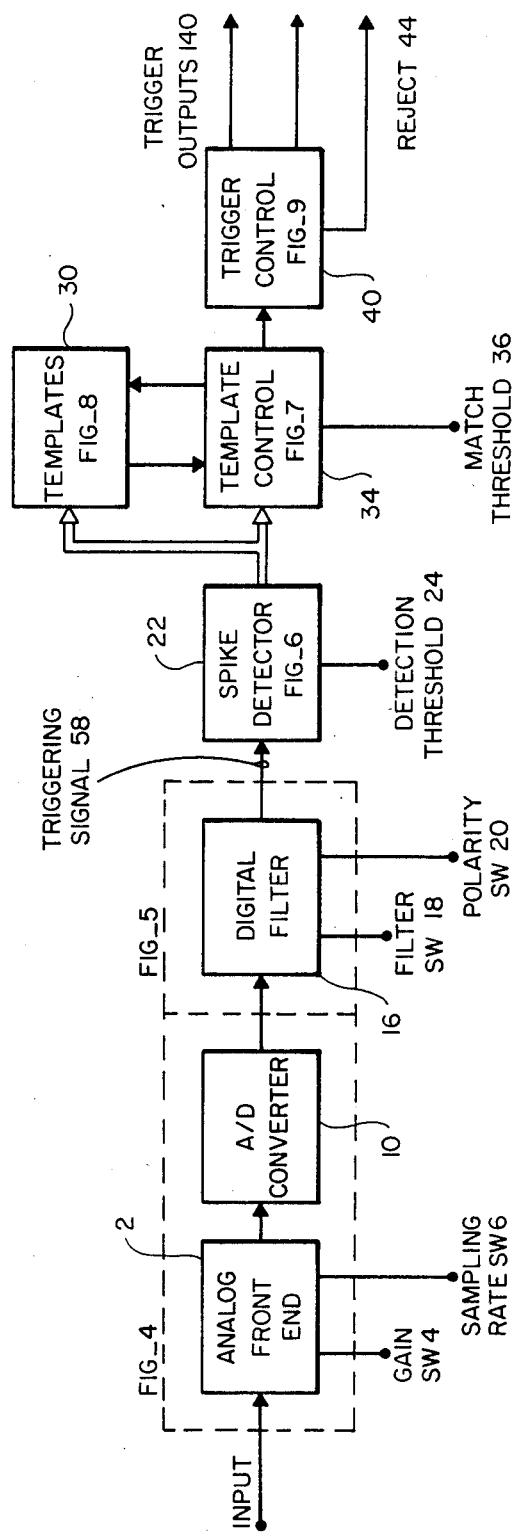
FIG_4

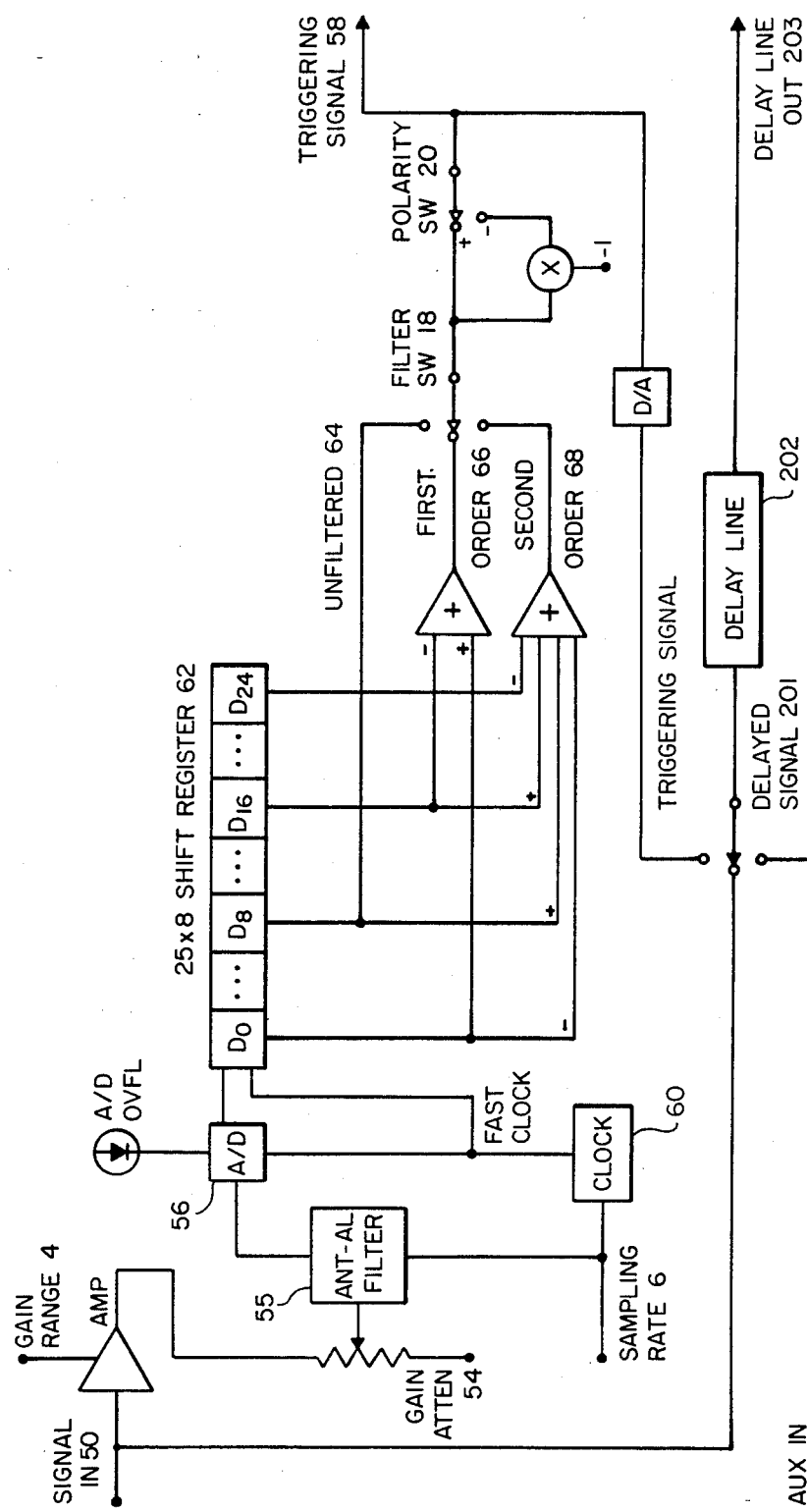
FIG_5

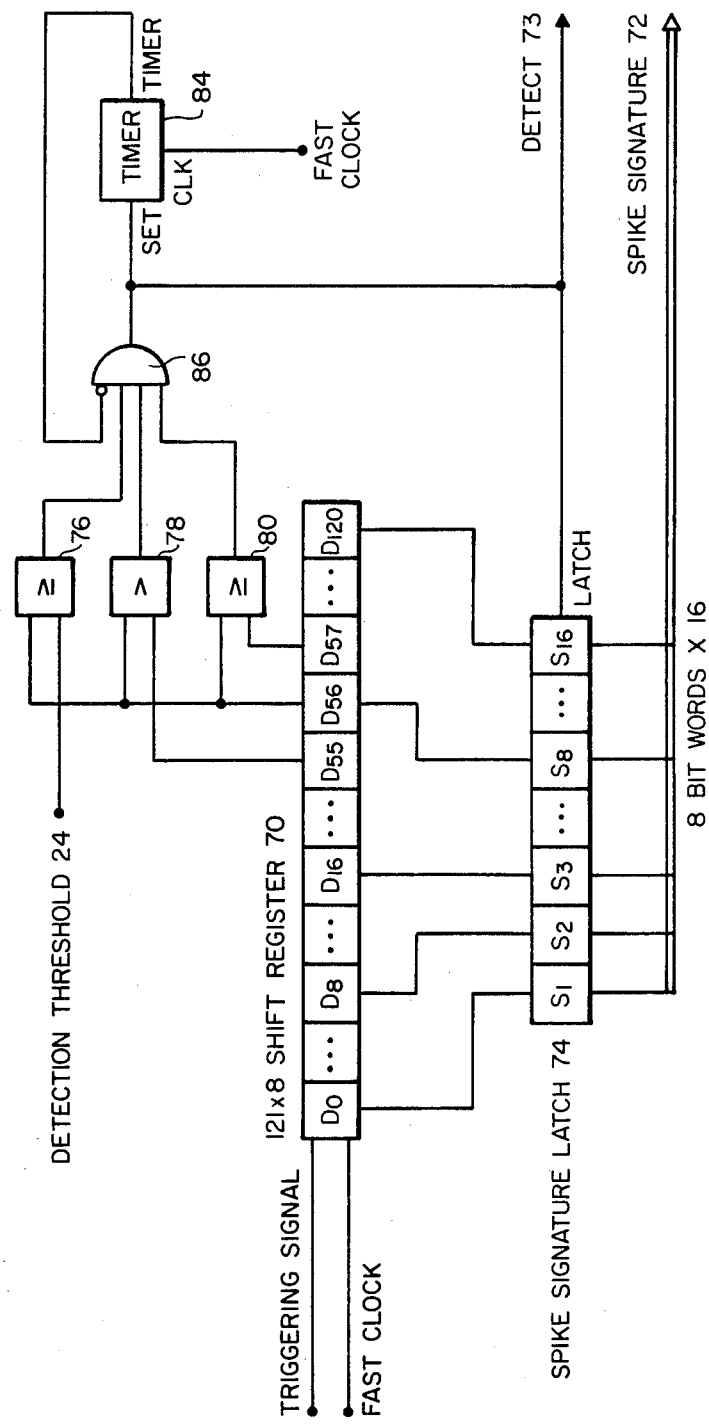
FIG_6

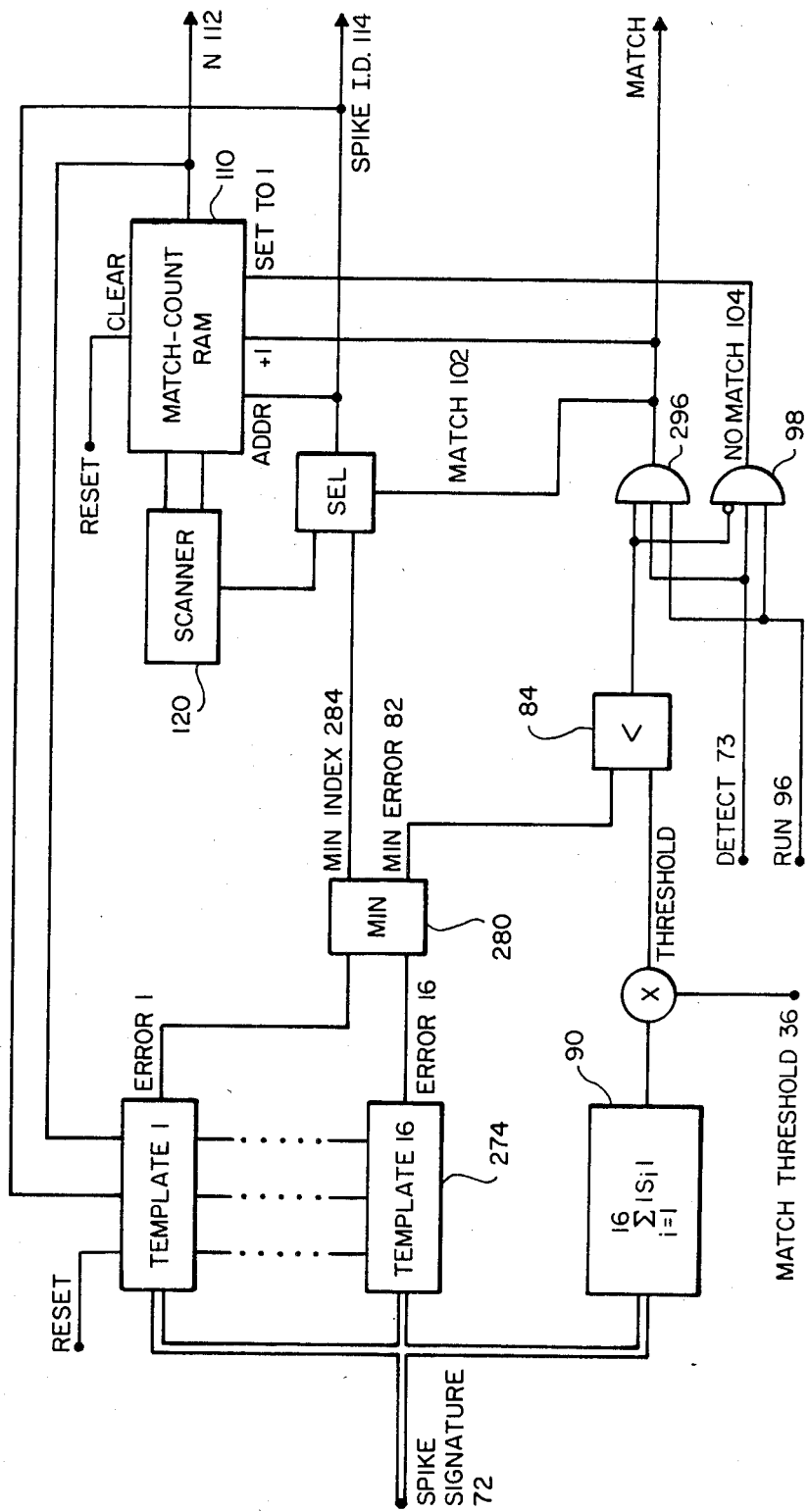
FIG_7

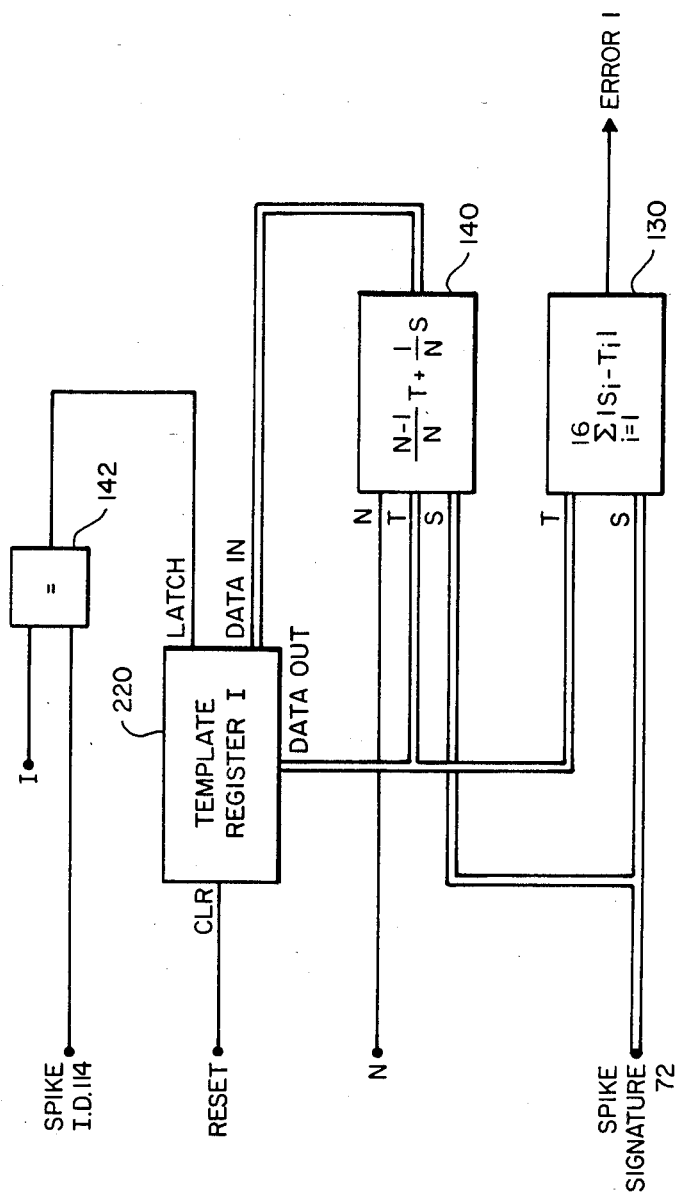
FIG_8

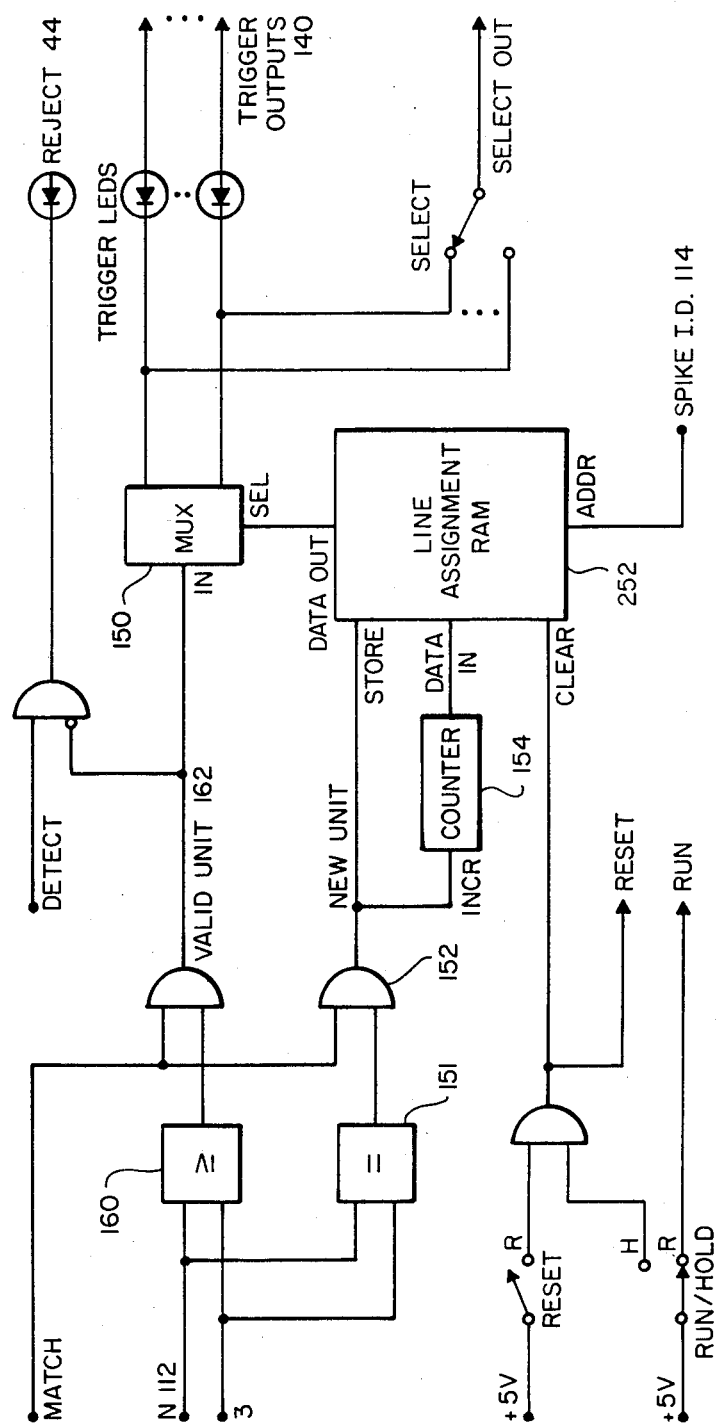
FIG_9

METHOD FOR REAL-TIME DETECTION AND IDENTIFICATION OF NEUROELECTRIC SIGNALS

This invention relates generally to the analysis of neuroelectrophysiological signals, and more particularly this invention relates to an improved method and apparatus for detecting and identifying individual nerve and muscle action potentials in electrical signals recorded from muscle, nerve, and brain.

Neuroelectric signals recorded by needles or microelectrodes are used experimentally to investigate the behavior of the nervous system and clinically to diagnose neuromuscular disorders. Such signals consist of trains of impulses called action potentials which reflect the electrical discharges of individual neurons or muscle fibers. The first step in analyzing the information contained in the signal is to detect the times at which these impulses occur. In the simplest case, there is a single action-potential train whose impulses must be detected in the presence of background noise. In the more complicated case, the electrode picks up discharges from more than one nearby cell, and the signal contains more than one action potential train. Often the additional action potentials are unwanted interference, although sometimes "multi-unit" signals are recorded intentionally to increase experimental yield or to study the comparative behavior of or the interactions between neighboring cells. In the multi-unit case, the detection problem includes the need to sort out the action potentials arising from the different units. This is possible because the action potentials from different cells usually differ in amplitude or shape due to their different geometrical configuration with respect to the electrode.

Presently, there are several commercially available devices, called "triggers" or "discriminators", for detecting action potentials in neuroelectric signals. They operate in real time, delivering a trigger pulse every time they detect an action potential which meets certain programmable criteria. As a rule, these devices are relatively simple, and as a result they tend to have only a limited ability to distinguish between different action potentials and to be somewhat unwieldly to use. This will be illustrated in the following two examples.

One type of trigger in current use is the "amplitude trigger" commonly used in single-fiber electromyography (as, for example, in the DISA 15G23 Delay Line, Disa Electronics, Copenhagen, Denmark). Single-fiber electromyography is a clinical technique used in diagnosing neuromuscular disorders which involves examination of muscle-fiber action potentials recorded using a special needle electrode inserted into a patient's muscle. The trigger is needed to stabilize the display of the action potential on an oscilloscope. The amplitude trigger commonly used in this application detects each time the input signal crosses a user-selected threshold. For signals with only one action potential train, the threshold is set to a level just higher than the amplitude of the baseline noise so that each action potential will generate a trigger pulse. For multi-unit signals, however, the amplitude trigger is only of limited usefulness; it can only be set to distinguish the largest action potential if there are more than one, and it is unable to distinguish between action potentials of the same size, regardless of their shapes. Also, even though the amplitude trigger has only two manual adjustments, the threshold level and the $+/-$ slope, the difficulty of having to continuously adjust these settings with one hand while manipulating the needle with the other is one of the reasons that the single-fiber examination is considered technically difficult and is not more widely performed.

A somewhat more sophisticated trigger is the "time-amplitude window discriminator" used in basic electrophysiology, for example the BAK model DIS-1 (BAK Electronics, Clarksburg, Md.). This device allows the user to specify a delay and an amplitude window as well as a threshold. When an action potential crosses the threshold, it waits for the specified delay period and then examines the action potential's amplitude, issuing a trigger pulse only if the amplitude falls within the specified window. The time-amplitude window discriminator essentially looks at two sample values of an action potential's waveform and so is more discriminating than the amplitude trigger. But it is very complicated to use; there are five controls which must be set by hand. In addition, these controls must be continuously adjusted throughout the analysis session if the shape of the action potential changes, as it often does because of electrode slippage or drift of physiological parameters.

Both of the above triggers lack the ability to track slow changes in spike shape caused by electrode slippage or physiological drift.

In addition to hardware discriminators, quite a number of computer programs for sorting spike trains have been developed. These generally run on lab minicomputers and require that the signals already be digitized and stored. Computer analysis offers much more power than the simple hardware discriminators. For one thing, sophisticated signal-processing algorithms can be used, allowing spikes to be distinguished very reliably on the basis of their entire waveforms rather than just one or two sample values. Moreover, the number of different action potentials which are present and their shapes can be determined automatically. This is a task which must be done by hand when using a hardware discriminator. Futhermore, slow changes in spike shape can be tracked adaptively, freeing the user from this arduous task.

Unfortunately, there are also two large disadvantages with computer analysis making it unattractive in many applications and unacceptable in others. First, it is quite expensive, both in terms of computation power and storage capacity. Second, it can only be done off line. This makes it unacceptable for clinical use, for example.

Until now there has been no bridge between the signal-processing power available using a general-purpose computer, and the speed available using a piece of special-purpose hardware.

Accordingly, an object of the present invention is an improved method of detecting and identifying action potentials in neuroelectrophysiological signals.

Another object of the invention is an automated apparatus for improved real-time detection and identification of action potentials in neuroelectrophysiological signals.

A feature of the invention is a fast digital filtering process for selecting action potentials from background activity and transforming them into sharp spikes which can be more easily detected and identified.

Another feature of the invention is a process for representing a spike's shape by a set of parsimoniously spaced and precisely registered sample values.

Another feature of the invention is a process for recognizing recurring spike shapes, storing templates of them, identifying subsequent spikes by comparing them with the templates, and adaptively updating the templates to track slow changes in the spikes.

Another feature of the invention is a process for delivering a trigger pulse on one of several output lines every time a spike is identified as matching one of the stored templates.

Briefly, in accordance with the invention, the neuro-electrophysiological signal is first sampled, digitized, and digitally filtered. The filtering accentuates the rising edges of the action potentials making them into sharp spikes which are easier to detect and identify. Each spike which exceeds an amplitude threshold is detected and characterized by a "signature" consisting of sixteen of its sample values taken at theoretically prescribed intervals and aligned precisely with respect to its peak. The signature is then compared with templates of previously detected spikes, and a trigger pulse is generated on the appropriate output line if it matches one of them. New templates are automatically formed when new spikes are detected, and old templates are continuously updated to track slow changes in spike shape.

The invention and objectives and features thereof will be more readily apparent from the following detailed description and appended claims when taken with the drawings.

FIGS. 1A and 1B illustrate the operation of the second-order low-pass differentiating filter in accordance with the disclosed embodiment of the invention.

FIGS. 2A and 2B illustrate action potentials with no filtering and with second order low pass differentiation.

FIGS. 3A–3C illustrate waveforms which are, respectively, misaligned due to out-of-phase samples, aligned by oversampling, and aligned by signatures in accordance with the disclosed embodiment of the invention.

FIG. 4 shows an exemplary embodiment of the Smart Trigger in block diagram form.

FIG. 5 shows details of the Analog Front End, A/D converter and Digital Filter of FIG. 3;

FIG. 6 shows details of the Spike Detector of FIG. 3;

FIG. 7 shows details of the Template Control of FIG. 3;

FIG. 8 shows details of the Template Storage and Update System of FIG. 3; and

FIG. 9 shows details of the Trigger Control of FIG. 3.

Real-time detection and identification of action potentials in accordance with the invention is accomplished by a device, hereafter called the "Smart Trigger," which is an intelligent, real-time trigger capable of automatically discriminating up to eight different spike waveforms on a single input channel and delivering trigger pulses on eight separate output lines.

The Smart Trigger allows optional first- or second-order differentiation (low-pass filtering) of the input signal as a pre-processing step. Such pre-processing often appreciably enhances spike detectability and discriminability: it flattens the signal baseline by suppressing low-frequency noise arising from distant units, artifact, and baseline drift, and at the same time it sharpens the spikes, increasing their temporal resolvability, improving their signal-to-noise ratios, and enhancing their distinguishability from spikes of other units.

FIGS. 1A and 1B illustrate how differentiation can improve spike detectability. FIG. 1A shows a typical signal to be analyzed, in this case a 0.5-s EMG interference pattern recorded from a healthy human biceps using a concentric needle electrode. FIG. 1B shows the same signal after second-order low-pass differentiation. The spikes can be seen to stand out very clearly from the flat baseline. The spikes corresponding to the six largest motor-unit action potentials have been identified by the algorithm used by the Smart Trigger.

FIGS. 2A and 2B show how spikes from different units are more easily distinguished after differentiation. FIG. 2A shows ten occurrences of each of three motor-unit action potentials from the unfiltered EMG signal of FIG. 1A FIG. 2B shows the same thirty potentials signals after second-order low-pass differentiation. The three units are much easier to tell apart after differentiation.

The following "low-pass differentiating" formulas are used to perform the differentiation:

First-order $Y_t = 32 x_{t+T} - x_{t-T}$
Second-order $Y_t = -x_{t+3T} + x_{t+2T} + x_{t+T} - x_{t-T}$
where:
x is the raw signal,
y is the filtered signal, and
T is the signal's Nyquist sampling interval (which will be discussed below).

These formulas are extremely fast, requiring only one and three additions (and no multiplications) per sample, respectively. They also have a desirable low-pass property which prevents undue accentuation of high-frequency noise.

The Smart Trigger of the present invention uses a threshold-crossing criterion to detect the spikes in the triggering signal. Each 16-sampling-interval-long segment of the triggering signal which contains at least one positive-going crossing of the spike-detection threshold is detected as a possible triggering event. We refer to these events as "spikes" since they usually appear spike-like and contain only one threshold crossing, and we call a spike which contains more than one threshold crossing a "polyphasic spike." Polyphasic spikes arise spuriously due to superimpositions, but they can also arise validly from a unit which discharges in a complex manner. For this reason, the Smart Trigger treats polyphasic spikes as single entities, in the same way as simple spikes.

The spike-detection threshold is user-selectable. This allows greater versatility than a hard-wired threshold would, even an adaptive one proportional to the standard deviation of the baseline noise. To facilitate setting the threshold, the Smart Trigger supplies a DC voltage proportional to the threshold for comparison with the triggering signal. A switch also allows the user to invert the polarity of the triggering signal if it contains primarily negative-going spikes.

The Smart Trigger uses a new method for representing a spike's waveform which allows maximum discrimination and at the same time is quite efficient. It represents a waveform by a "signature" consisting of 16 sample values spaced according to the spike's Nyquist rate and registered so that the eighth sample corresponds precisely with the spike's peak. (A waveform's Nyquist rate equals two times the frequency of its highest frequency component and is theoretically the lowest sampling rate needed to completely capture all the information it contains). The Nyquist rate for a particular application must be set by the user, and it should be set so that the sampling interval is about half the risetime of the fastest spikes. The Smart Trigger determines the signature by first oversampling the waveform at eight times the selected rate in order to locate the peak with high temporal resolution, and by then keeping only every eighth sample.

This method of representing spike waveforms has two advantages. First, it uses all the information available about the waveform's shape, and thus allows for the greatest possible discrimination between different waveforms. There are other representation methods which require fewer samples and subsequently fewer computations in operations such as template comparisons for example sets of features such as amplitude and duration or principal-component coefficients, but they make a priori assumption about waveshape and can give poor discrimination between spikes which are atypical. The Smart Trigger uses the full sample-value representation instead because of its greater generality.

The second advantage of the signature is that it implicitly solves the problem of waveform alignment. Two waveforms must be aligned very precisely before they can be accurately compared. They are often aligned by maximizing their cross correlation, but it is known that for sharp spikes such as those in the Smart Trigger's triggering signal, peak-to-peak alignment works almost as well. This is important because it means that a spike can be registered by its peak when it is first detected, a computationally simple operation which can be done without reference to any other spike. The spike can then compared to other registered spikes without further alignment. For full accuracy, it is known that the peak must be located with a resolution of 0.2 to 0.125 of the Nyquist sampling interval. The Smart Trigger achieves this resolution by oversampling and finding the largest sample. Once the proper registration is established, the additional samples are discarded since they contribute no new information. In this way the Smart Trigger differs from most previous template matching schemes which have either suffered from poor temporal resolution due to Nyquist rate sampling or from inefficiency due to superfluous data.

FIGS. 3A, 3B and 3C illustrate the concept of the signature. FIG. 3A shows two spikes from the same motor-unit, represented by sixteen samples at 10 kHz. The spikes appear different because the samples are out of phase. FIG. 3B shows the same two spikes represented by 128 samples at 80 kHz and aligned with high temporal resolution. The spikes are now seen to be quite similar. FIG. 3C shows the same two spikes represented by their signatures obtained in accordance with this invention by keeping only every eighth sample of the waveforms of FIG. 3B. This representation offers both high temporal resolution and low data rates.

The Smart Trigger sorts the spike signatures using the template-matching method. It has 16 registers in which to store templates of the new spike signatures it detects. Since superimpositions can give rise to spurious signatures, it waits until it detects a signature at least three times before considering it a "valid unit signature". In order to track slow changes, it updates a template each time it detects a signature which matches it. When all the registers are full, those which do not contain valid unit signatures are recycled as needed.

Signatures are compared using the absolute error metric, i.e. the sum of the absolute differences between the sample values. This metric can be computed more quickly than the familiar squared-error metric, and it can be shown to give comparable performance. The criterion for a match is that the absolute error be less than a certain fraction of the area of one of the signatures. The fraction 30% is recommended, but the user is able to select a stricter or looser criterion to suit a particular signal to noise ratio. An area-dependent threshold gives better performance than an absolute one because larger spikes can tolerate more noise than smaller ones. The Smart Trigger does not attempt to resolve superimpositions since techniques for doing so are prohibitively time-consuming.

The Smart Trigger delivers trigger pulses in the following way. It assigns each valid unit signature to one of its eight output lines, and delivers a trigger pulse on that line whenever it detects a spike with that signature. The rising edge of the trigger pulse corresponds precisely with the peak of the signature, although it lags it by several ms due to computation time. A delay line is provided so that the input signal, the triggering signal, or an auxiliary signal can be synchronized with the trigger pulse.

The Smart Trigger can be implemented using digital electronic components. The block diagram and major manual controls of the Smart Trigger are shown in general in FIG. 4 and in greater detail in FIGS. 5-9.

The analog front end 2 consists of a variable amplification/attenuation stage controlled by a GAIN switch 4, and an anti-alias filter whose low-pass cutoff is controlled by a sampling-rate switch 6. The conditioned analog signal is sampled by the 8-bit A/D converter 10 at the rate of eight times the Sampling-rate switch 6 setting. The sampled signal is then processed by a digital filter 16 which either passes the signal itself or computes its first or second derivative, according to the filter switch 18 setting, and which inverts the signal if so selected by the polarity switch 20. The output of the digital filter 16 is called the "triggering signal" 58.

The triggering signal is processed by the spike detector 22, which looks for crossings of the threshold selected by the detection threshold knob 24. When a spike is detected, the detector determines the spike's peak sample, decimates the triggering signal by a factor of eight, and extracts 16 of the decimated samples, seven before and eight after the peak. These 16 samples constitute the spike's signature. Notice that the signature has an effective sampling rate equal to the sampling rate switch 6 setting, and that it is precisely registered so that its peak occurs on the eighth sample.

The incoming spike signatures are then compared to the templates in the template registers 30. Each register computes the absolute error between the incoming signature and its template. The template control section 34 polls the registers to determine the smallest error and compares it to the threshold selected by the match threshold dial 36. If the incoming signature matches one of the templates, the template control section 34 updates that template by averaging in the new signature. If this is the template's third match, the next available trigger out line 140 is assigned to the template by trigger control 40. If the template already has a trigger out line assigned to it, a trigger pulse is generated on that line. If the incoming signature does not match any of the templates, the reject LED 44 is pulsed and the signature is stored in the next available template register, with the registers of unmatched templates being recycled as necessary.

Turning to the detailed block diagrams, the signal to be analyzed is applied to the input labeled signal in 50 which is an input to one stage of amplification whose gain is controlled by the gain range switch 4. The signal may also have its gain attenuated according to the gain atten potentiometer 54. The input signal should be in about the + or −5 volt range as the Smart Trigger provides only limited amplification or attenuation. The signal is then applied to an analog anti-aliasing filter 55 whose low-pass cutoff is controlled by the sampling rate switch 6. The signal is then applied to an A/D converter 56 to be digitized in accordance with known principles at a rate determined by clock 60. The sampling rate is set to eight times the nominal sampling rate, which is selected by a sampling rate switch 6 which is a five position rotary switch.

The possible nominal sampling rates, in kHz, in this preferred embodiment (and anti-alias filter low-pass cutoffs, also in kHz) are 1.0(0.5), 2.0 (1.0), 5.0 (2.5), 10.0 (5.0), and 20.0 (10.0). The sampling rate is called nominal because although the spike signatures effectively have this sampling rate for computational and storage purposes, the input signal is actually sampled at eight times this rate by the A/D converter. This is in order to allow high resolution registration, as explained fully above. As will become apparent from the discussion of FIG. 6, (the spike detector), the effective sampling rate will later be reduced by a factor of eight in developing the spike signature. For optimal performance the nominal sampling rate set by rate switch 6 should be set so that the nominal sampling interval is about half the rise time of the fastest spikes.

The output of the A/D converter 56 is shifted into a shift register 62 whose outputs are used to provide either an unfiltered output 64, a first-order differentiated output 66 or a second-order differentiated output 68. The first and second order derivatives are provided by adding and substracting various samples of the signals according to the equations discussed above. Any one of the three outputs can be selected by filter switch 18. The output of the digital filter is called the triggering signal 58. The polarity switch 20 selects whether the triggering signal is inverted or noninverted. As designed, and shown in this preferred embodiment, the Smart Trigger system detects and operates on only positive spikes; therefore, the signal should be inverted if it contains primarily negative spikes.

The delay switch 201 may apply either signal in, aux in, or the triggering signal (after D/A conversion) to a delay line 202 whose delay matches the computational delays that occur between the occurrence of a spike's peak and the rising edge of the trigger out pulse. The exact delay depends on the sampling rate setting.

Referring now to the spike detector shown in FIG. 6, the objective of this circuitry is to detect a peak in the sampled data stream which exceeds a specified amplitude threshold, and, upon detecting such a peak, to extract from the data stream sixteen samples which stand in a precise temporal relationship to the peak. The peak indicates the occurrence of a spike of interest in the input signal, and the sixteen samples fully characterize the spike, as described above. The sixteen samples are called the spike's signature.

The occurrence of a peak exceeding the threshold is detected in the following way. The sampled data is passed through the shift register 70 which holds at any time the 121 most recent samples. Two comparators 78 and 80 determine when position 56 of the shift register contains a peak, that is when the sample in position 56 is greater in amplitude than either of its two neighbors. Another comparator 76 determines when the sample in position 56 is greater in amplitude than the threshold set by the detection threshold potentiometer 24. This detection threshold potentiometer should be set to a level higher than the baseline noise so that only peaks which rise out of the noise level will be detected. The and gate 86 determines when both these conditions are met, that is when there is a peak in position 56 which exceeds the threshold, and it issues the detect signal 73 when this situation occurs. A fourth input to the and gate 86 is provided by the timer 84 to prevent more than one peak from being detected during a specified time interval. This is to prevent generating more than one detect signal for a complex spike with multiple peaks. Specifically, when a peak is detected, the timer 84 is set, and it then inhibits gate 86 until a sufficient time has elapsed so that all the data which was in the shift register 70 at the time of the detection has been shifted out. It should be noted that a peak in the data stream will not be detected until it reaches position 56 of the shift register. It should also be noted that this circuitry does not detect the globally highest peak which is in the shift register 70 at any given time; rather, in the case of a complex spike with more than one peak, it detects only the first of the peaks which exceeds the detection threshold.

When the detect signal 73 occurs, signalling the detection of a spike, the sixteen samples constituting the spike's signature are obtained by latching into the spike signature latch 74 every eighth sample from the shift register 70. As shown in FIG. 6, the peak sample from position 56 of the shift register becomes latched into position 8 of the latch, and the other positions of the latch are supplied by shift register positions spaced eight positions apart, that is spaced according to the nominal sampling interval. Notice that this step effectively reduces the sampling rate since seven of every eight samples are discarded when the data is transferred from the shift register 70 to the latch 74. Notice however that the peak could not have been located as precisely without first sampling the data at the faster rate.

The sixteen samples constituting the spike signature are presented on the spike signature bus 72 for comparison with the templates as will be discussed in reference to FIG. 7. It is critical to note that positioning the precise peak sample as the eighth sample in the spike signature 72 will allow accurate alignment of the spike signature with every template signature with which it is to be compared. That is every template with which it may usefully compare will also have its precise peak sample in the eighth position.

Referring to FIG. 7, the purpose of the circuitry shown in this figure is to identify the current spike signature. That is, the spike signature is compared with each of the stored template signatures, and if it matches one of them its identity is the index of the template it matches, while if it does not match any of them then it will be used as a new template itself. Specifically, the spike signature 72 is compared to all the template signatures each of which comprises sixteen eight bit words having a peak in the eighth word position. The details of each of the template circuits 274 are described in greater detail with respect to FIG. 8. But is apparent from FIG. 7 that each template signature is compared to the single spike signature, and an error signal is generated representing the difference between the spike signature and each template signature. The sixteen error signals are provided to a minimum error detector 280 which detects which of the comparisons results in the least error, that is which of the templates gives the best match to the spike. Each template 274 has the circuitry as will be discussed in FIG. 8 to make this comparison and develop this error signal, so that the sixteen comparisons are carried out substantially simultaneously. Each error signal equals the sum of the absolute differences of the components of the spike signature and the template signature. Thus this value of any error signal will be small if the spike signature and the template signature match and large if they do not match. We wish to detect the smallest error.

Returning to the minimum error detector 280, it selects and puts out two values: a min error signal 82 which is the minimum of the error signals resulting from the comparisons between the spike signatures and the sixteen template signatures, and a min index signal 284 which identifies exactly which of the templates achieved the minimum error in the comparison. To detect if the error is sufficiently small to make a good match, the spike signature 72 is also fed to a circuit 90 which establishes the sum of the components of the signature, representing the entire area under the curve represented by the signature. This value is applied to a multiplier along with the input from a match threshold potentiometer 36. This potentiometer sets the similarity threshold which determines how far a spike signature can differ from a template and still be considered a match. The recommended dial setting in the preferred embodiment is 30%, but the user can choose a stricter or looser threshold to suit a particular signal to noise ratio. Thus for example with a setting of 30%, the minimum error signal 82 must be less than 30% of the area of the spike signature for a match to be declared.

The spike detect signal from the circuitry of FIG. 6 is now applied along with a positive indication from the output of the threshold comparitor 94 and a signal from the hold run switch 96 to two gates 296, 98. Gate 296 generates the match signal 102 to indicate the occurrence of a spike which matches a template, while gate 98 generates the no-match signal 104 to indicate the occurrence of a spike which fails to match any of the templates. The hold run switch is a two position switch controlling the Smart Trigger's operating mode. In the run mode, the Smart Trigger performs its normal function of detecting spikes and delivering trigger out pulses; in the hold mode, the Smart Trigger ceases delivering trigger out pulses and stops attempting to form new templates, although it retains the templates it has acquired. When data is being analyzed from tape, the hold mode allows the user to pause while changing reels or rewinding the tape after a preliminary training pass. The match count ram 110 is provided to keep track of the number of matches which have been detected for each of the templates. This is important because templates are often formed for noise spikes and spikes resulting from superimpositions, and the only way to distinguish a template corresponding to a valid unit from a template formed by chance is on the basis of the number of matches. Spikes from a valid unit occur often and so the template which corresponds to them will be matched many times, while a random spike will never recur, and so its template will be unmatched.

The operation of the match count ram 110 depends on whether the current spike signature matched one to the template signatures or not. In the case of a match, i.e. when the match signal 102 is active, then the index of the matching template 284 is applied to the ram and the number of matches associated with this template is looked up. This number is incremented by one to record the fact that a new match has been detected, and it is put out on the line N 112 for use in updating the template, as will be discussed in reference to FIG. 8, and for use in assigning trigger out lines and generating the trigger pulse, as will be discussed in reference to FIG. 9. The index of the matching template is also put out on the spike ID line 114 for these same purposes.

In the case that no match was found, i.e. that the no match signal 104 is active, then the scanner 120 will search through the values stored in the match count ram to select a template which has been matched the least number of times. This template will then be thrown out and replaced by the new spike signature 72 as explained in FIG. 8. The reason for this is that the new signature may well correspond to a new action potential and so we would like to form a template of it. The old template, on the other hand, since it has so few matches probably corresponded to a random noise spike and can be safely thrown out. In this no-match case, the count associated with the selected template in the match count ram 110 is set to 1 and the spike ID line 114 is set to the index of the selected template.

FIG. 8 represents the circuitry associated with each of the sixteen templates 274. The circuitry of FIG. 8 includes a register 220 comprising sixteen eight bit words which holds the presently stored template signature. The circuitry must perform two functions: first it must calculate the error signal which it does by comparing the incoming spike signature 72 with the template signature presently stored in register 220. The error is calculated by computing the absolute differences of the components of the two signatures in device 130 according to the indicated formula and putting out the error signal representing the results of this calculation.

The second function which the template circuitry must perform is the updating of the template signature, which is performed in updating device 140. Two cases must be considered: (1) If a match has been achieved, as will be indicated by a value of the input N 112 which is greater than 1, then some slight modification of the template signature presently stored is desirable in case the signature has changed slightly due for example to slippage of the electrode. This adaptability of the template signatures is a very important advantage of the present invention, and is achieved through the formula which forms the basis of the device 140. (2) Alternatively, if no match has been achieved, (that is if this is the first time a spike with this signature has been detected), then the term $N-1$ in device 140 drops out, and the present spike signature is stored directly in the template register 220. The latch line is turned on when the spike ID signal 114 from the template control matches the template index indicated on line I. The gating is accomplished by device 142 and is to insure that the correct template is updated.

Turning to FIG. 9, the trigger control circuitry is used to supply trigger pulses on the eight trigger out lines 140 to indicate the detection of spikes which match the templates which have been identified as corresponding to valid units. The trigger control also pulses the trigger LED indicators 141 to provide a visual display of how many valid units have been identified and how often these units are being detected. It also pulses the reject LED 44 to indicate the detection of a spike which does not correspond to a valid unit.

It has already been mentioned that superimpositions and spurious noise pulses get stored as templates, and that it is necessary to decide which templates correspond to valid units. It is also necessary, since there are sixteen templates but only eight trigger outlines, to assign the trigger out lines only to the templates which correspond to valid units.

The decision whether or not a template corresponds to a valid unit is based on the number of matches which have been detected for the template. In this preferred embodiment, there must have been at least three matches to establish validity. This requirement is checked by comparators 160 and 151 which compare the number N 112 which is the match count for the template corresponding to the current spike with the constant 3. In conjunction with the match signal 102 from FIG. 7, these comparators generate the valid unit signal 162 when the count N in greater than or equal to three and the new unit signal 152 when the count is exactly equal to three.

The assignment of the trigger out lines is accomplished by the line assignment ram 152 and associated circuitry. The line assignment ram 151 keeps track of which line has been assigned to each template. A new assignment is made in the following way. The counter 154 keeps track of how many lines have already been assigned. When a new unit is first validated, as indicated by the new unit signal 152, then the counter 154 is incremented by one, and its value, which indicates the next available output lines, is stored into the ram in the position associated with the template corresponding to the current spike, whose index appears on the spike ID line 114. After this, whenever a spike matching this template is detected, the ram 252 will put out the number of this output line. The number is used to direct the multiplexer 150 to steer the valid unit signal 162 to the appropriate trigger out line so as to generate the desired trigger pulse.

In summary, the present invention is an intelligent real-time trigger capable of automatically discriminating up to eight different spike waveforms appearing on a single input channel and delivering trigger pulses on eight separate output lines. It is highly useful in sorting action potentials form multi-unit nerve and muscle signals. The system can be set to trigger off the input signal itself or on the first or second derivative. The differentiation is provided to improve triggering performance by flattening the signal baseline and sharpening the spikes so that they can be more reliably discriminated.

Other alternatives to the present invention and specific features thereof may be found by one of skill in the art who has studied the above invention disclosure. Therefore, the scope of the present invention is to be limited only by the following claims.

What is claimed is:

1. A method of real time analysis of neuroelectrophysiological signals for detecting and identifying action potentials comprising the steps of digitally filtering the signals using a low-pass differentiator and automatically detecting and identifying the recurring spikes in the filtered signal.

2. A method as claimed in claim 1 wherein said identifying step includes the step of issuing a trigger pulse on one of a plurality of output lines to indicate the identity of the detected action potential.

3. A method as claimed in claim 1 wherein the step of digitally filtering the neuroelectrophysiological signal compares the filtered neuroelectrophysiological signal to an assigned threshold value, the spikes representing action potentials exceeding the threshold.

4. A method as claimed in claim 3 wherein the detecting step includes dividing the action potential signal into intervals, wherein each interval contains one of said spikes, and assigning a signature to each signal interval.

5. A method as claimed in claim 4 wherein said signal intervals are disjoint and do not overlap.

6. A method as claimed in claim 4 including the step of comparing each signal signature to a plurality of stored signatures stored as templates, and indicating the closest match between signal and template signature.

7. A method as claimed in claim 6 including the step of adapting the template indicated as the closest match to the signal signature to improve the template's signal to noise ratio and to track slow changes in signature configuration.

8. A method as claimed in claim 7 including calculating the error differential between the signal signature and the template indicated as the closest match, comparing the differential error to a stored threshold error value, and inhibiting the output if the error differential exceeds the stored error threshold level.

9. A method as claimed in claim 8 further comprising the steps of replacing the template having a stored history of the fewest previous matches with the signal signature in response to the indication of error differential exceeding the threshold value.

10. A method as claimed in claim 8 further comprising the steps of replacing the template having a stored history of the fewest previous matches with the signal signature in response to the indication of error differential exceeding the threshold value.

11. A method as claimed in claim 6 wherein each of said signal signatures and template signatures comprises an equal number of words, said process further comprising the step of aligning said spike signature for comparison with the template signatures by centering the word representing the peak value of the neuroelectrophysiological signal in said interval.

12. A method as claimed in claim 11 including the steps of initially sampling the neuroelectrophysiological signals at a rate fast enough to locate the peaks with high temporal resolution, and then decimating the samples to obtain said signal signature, keeping only the theoretically minimum number of samples needed to characterize the signal signature.

13. A method as claimed in claim 11 wherein said process further includes the step of simultaneously comparing the signal signature with a plurality of said template signatures.

14. A method as claimed in claim 13 wherein said digitally filtering step includes a low pass differentiating of the action potential signal utilizing a formula having only additive terms in the algorithm.

15. A method as claimed in claim 14 wherein said digital filtering step comprises developing a first order differential of the signal according to the formula $$Y_t = X_{t+T} - X_{t-T}$$

where
X is the raw signal,
Y is the filtered signal,
T is the signal's Nyquist sampling interval.

16. A method as claimed in claim 15 wherein said digital filtering step comprises developing a second order differential of the signal according to the formula $$Y_t = -X_{t+3T} + X_{t+2T} + X_{t+T} - X_{t-T}$$

where

X is the raw signal,

Y is the filtered signal,

T is the signal's Nyquist sampling interval.

17. A method as claimed in claim 13 including the step of adapting the template indicated as the closest match to the signal signature to reflect the actual signature.

18. A method as claimed in claim 17 including calculating the error differential between the signal signature and the template indicated as the closest match, comparing the differential error to a stored threshold error value, and inhibiting the output if the error differential exceeds the stored error threshold level.

19. A method as claimed in claim 17 wherein each of said signal signatures and template signatures comprises an equal number of words, said process further comprising the steps of aligning said spike signature for comparison with the template signature by centering the word representing the peak value of the signal in the signal signature.

20. A method as claimed in claim 19 wherein said process further includes the steps of simultaneously comparing the signal signature with a plurality of said template signatures.

21. A method of real time analysis of neuroelectrophysiological signals for detecting and identifying action potentials comprising the steps of digitally filtering the signal, and detecting and identifying the recurring spikes in the filtered signal by (a) detecting as a spike each interval containing a peak whose amplitude exceeds a known threshold, (b) matching each detected spike with one of a plurality of stored spike templates, and (c) indicating the result of said matching step.

* * * * *